US011712234B2

(12) United States Patent
Jones et al.

(10) Patent No.: US 11,712,234 B2
(45) Date of Patent: Aug. 1, 2023

(54) FIXED SUTURE CONSTRUCT FOR SOFT TISSUE RECONSTRUCTION

(71) Applicant: Biomet Manufacturing, LLC, Warsaw, IN (US)

(72) Inventors: Austin Taylor Jones, Mesa, AZ (US); Christopher M. Palese, Warsaw, IN (US); Kevin N. Baird, Scottsdale, AZ (US); Hoang Nguyen, Litchfield Park, AZ (US); Carissa Henriksen, Scottsdale, AZ (US); Lindsay Mitchell, West Chester, PA (US)

(73) Assignee: Biomet Manufacturing, LLC, Warsaw, IN (US)

(*) Notice: Subject to any disclaimer, the term of this patent is extended or adjusted under 35 U.S.C. 154(b) by 161 days.

(21) Appl. No.: 17/131,122

(22) Filed: Dec. 22, 2020

(65) Prior Publication Data

US 2021/0196258 A1 Jul. 1, 2021

Related U.S. Application Data

(60) Provisional application No. 62/954,043, filed on Dec. 27, 2019.

(51) Int. Cl.
A61B 17/04 (2006.01)

(52) U.S. Cl.
CPC .. A61B 17/0401 (2013.01); A61B 2017/0412 (2013.01); A61B 2017/0459 (2013.01); A61B 2017/0464 (2013.01)

(58) Field of Classification Search
CPC ........ A61B 17/0401; A61B 2017/0412; A61B 2017/0459; A61B 2017/0464;
(Continued)

(56) References Cited

U.S. PATENT DOCUMENTS 10,034,663 B1 7/2018 Nason et al.
2008/0147063 A1* 6/2008 Cauldwell .......... A61B 17/0487
606/60

(Continued)

FOREIGN PATENT DOCUMENTS

EP 0634142 3/1998
EP 2879591 3/2018

OTHER PUBLICATIONS

"European Application Serial No. 20216339.0, Response filed Apr. 20, 2022 to Extended European Search Report dated Sep. 17, 2021", 23 pgs.

(Continued)

Primary Examiner — Shaun L David
Assistant Examiner — Rachael L Geiger
(74) Attorney, Agent, or Firm — Schwegman Lundberg & Woessner, P.A.

(57) ABSTRACT

Disclose herein are suture anchor constructs. The suture anchor constructs can include an anchor, a first suture, and a second suture. The anchor can include a post and a body. The body can define a central hole extending from a trailing end of the body along a central axis towards a leading end of the body. The first suture can have a first tail, a second tail, and a first intermediate portion located proximate the post. The second suture can have a third tail, a fourth tail, and a second intermediate portion secured to the post. The first, second, third, and fourth, tails can pass through the central hole.

13 Claims, 11 Drawing Sheets

(58) Field of Classification Search
CPC .... A61B 2017/0403; A61B 2017/0406; A61B 2017/0414; A61B 2017/0446; A61B 2017/0448; A61B 2017/045; A61B 2017/0451; A61B 2017/0458
See application file for complete search history.

(56) References Cited

U.S. PATENT DOCUMENTS

| | | |
|---|---|---|
| 2010/0292732 A1 | 11/2010 | Hiratsuka et al. |
| 2012/0109196 A1 | 5/2012 | Mccaw et al. |
| 2012/0179199 A1 | 7/2012 | Hernandez et al. |
| 2012/0290003 A1* | 11/2012 | Dreyfuss ............ A61B 17/0401 606/232 |
| 2013/0261664 A1 | 10/2013 | Spenciner et al. |
| 2014/0081325 A1 | 3/2014 | Sengun |
| 2016/0157851 A1* | 6/2016 | Spenciner ............ A61F 2/0811 606/232 |

OTHER PUBLICATIONS

"European Application Serial No. 20216339.0, Extended European Search Report dated Sep. 17, 2021", 12 pages.

* cited by examiner

FIXED SUTURE CONSTRUCT FOR SOFT TISSUE RECONSTRUCTION

PRIORITY CLAIM

This application claims priority to U.S. Provisional Patent Application No. 62/954,043, entitled "Fixed Suture Construct for Soft Tissue Reconstruction," filed on Dec. 27, 2019, the content of which is hereby incorporated in its entirety.

FIELD OF THE DISCLOSURE

The present disclosure relates to sutures. Specifically, the present disclosure relates to fixed sutures for soft tissue reconstructions and methods of use thereof.

BACKGROUND

Arthroscopic procedures often include sutures and anchors to secure soft tissue to bone. Despite their widespread use, sutures and suture anchors, as well as methods for their use, can be improved. For example, tying sutures to anchors can be very time consuming and difficult to perform. As a result, the cost of the procedure can be increased and the capacity of the surgeon can be limited. Current suture anchor constructs can include a sliding suture that usually requires a surgeon to tie knots in order to fix the suture to the anchor.

The systems and methods disclosed herein address the issues with sliding sutures.

SUMMARY

To better illustrate the systems and methods disclosed herein, a non-limiting list of examples is provided here.

Example 1 is a suture anchor construct comprising: an anchor including a post and a body, the body defining a central hole extending from a trailing end of the body along a central axis towards a leading end of the body; a first suture including a first tail, a second tail, and a first intermediate portion, the first intermediate portion located proximate the post, the first and second tails passing through the central hole; and a second suture having a third tail, a fourth tail, and a second intermediate portion, the second intermediate portion secured to the post, the third and fourth tails passing through the central hole.

In Example 2, the subject matter of Example 1 optionally includes wherein the second intermediate portion is located in between the post and the first intermediate portion.

In Example 3, the subject matter of any one or more of Examples 1-2 optionally include wherein the first intermediate portion is located in between the post and the second intermediate portion.

In Example 4, the subject matter of any one or more of Examples 1-3 optionally include wherein the second intermediate portion secured to the post includes the second intermediate portion forming a hitch knot.

In Example 5, the subject matter of Example 4 optionally includes wherein the hitch knot includes a sliding knot.

In Example 6, the subject matter of any one or more of Examples 1-5 optionally include wherein the second intermediate portion secured to the post includes the second intermediate portion forming a loop that is wrapped around the post and the third and fourth tails passing through the loop.

In Example 7, the subject matter of any one or more of Examples 1-6 optionally include wherein the post defines a through hole, the second suture passing through the through hole and tied into a knot located at a distal end of the through hole.

In Example 8, the subject matter of any one or more of Examples 1-7 optionally include wherein the post includes a barb, the barb passing through the second intermediate portion.

In Example 9, the subject matter of any one or more of Examples 1-8 optionally include wherein the post includes a first portion and a second portion located in between the first portion and the trailing end of the body, the second intermediate portion wrapped around the first portion.

In Example 10, the subject matter of any one or more of Examples 1-9 optionally include wherein the second intermediate portion secured to the post includes the second intermediate portion partially surrounding the post.

In Example 11, the subject matter of any one or more of Examples 1-10 optionally include a plug configured to fit into the central hole, the plug including first and second passages, the first tail passing through the first passage and the second tail passing through the second passage.

In Example 12, the subject matter of any one or more of Examples 1-11 optionally include a pin passing through the second intermediate portion proximate the post.

In Example 13, the subject matter of any one or more of Examples 1-12 optionally include a tube located proximate the post, the third and fourth tails passing through the tube.

In Example 14, the subject matter of any one or more of Examples 1-13 optionally include wherein the first suture is secured to the post.

Example 15 is a suture anchor construct comprising: an anchor including a post and a body, the body defining: a central hole extending from a trailing end of the body along a central axis; and a radial hole located proximate a leading end of the body and passing through the body, the post extending from a first portion of the radial hole to a second portion of the radial hole; a first suture including a first tail, a second tail, and a first intermediate portion, the first intermediate portion located proximate the post, the first and second tails passing through the central hole; and a second suture including a third tail, a fourth tail, and a second intermediate portion, the second intermediate portion forming a hitch knot that fixedly secures the second suture to the post, the third and fourth tails passing through the central hole.

In Example 16, the subject matter of Example 15 optionally includes wherein the second intermediate portion is located in between the post and the first intermediate portion.

In Example 17, the subject matter of any one or more of Examples 15-16 optionally include wherein the first intermediate portion is located in between the post and the second intermediate portion.

In Example 18, the subject matter of any one or more of Examples 15-17 optionally include wherein the hitch knot includes the second intermediate portion forming a loop that is wrapped around the post.

In Example 19, the subject matter of any one or more of Examples 15-18 optionally include wherein the hitch knot includes a sliding knot.

In Example 20, the subject matter of any one or more of Examples 15-19 optionally include wherein the post defines a through hole, the second suture passing through the through hole, the hitch knot located at a distal end of the through hole.

In Example 21, the subject matter of any one or more of Examples 15-20 optionally include wherein the first suture passes through the hitch knot.

In Example 22, the subject matter of any one or more of Examples 15-21 optionally include wherein the post includes a barb, the hitch knot tied to the barb.

In Example 23, the subject matter of any one or more of Examples 15-22 optionally include wherein the first suture is secured to the post.

Example 24 is a suture anchor construct comprising: an anchor having a post and a body defining: a central hole extending from a trailing end of the body along a central axis, and a radial hole located proximate a leading end of the body and passing through the body, the post extending from a first portion of the radial hole to a second portion of the radial hole; a first suture having a first tail, a second tail, and a first intermediate portion located proximate the post, the first and second tails passing through the central hole, and a second suture having a third tail, a fourth tail, and a second intermediate portion secured to the post, the third and fourth tails passing through the central hole.

In Example 25, the subject matter of Example 24 optionally includes wherein the post includes a first portion and a second portion located in between the first portion and the trailing end of the body, the second intermediate portion wrapped around the first portion.

In Example 26, the subject matter of any one or more of Examples 24-25 optionally include wherein the second intermediate portion secured to the post includes the post having a barb that passes through the second intermediate portion.

In Example 27, the subject matter of any one or more of Examples 24-26 optionally include wherein the second intermediate portion secured to the post includes the second intermediate portion partially surrounds the post.

In Example 28, the subject matter of any one or more of Examples 24-27 optionally include a plug configured to fit into the central hole, the plug includes first and second passages, the first tail passing through the first passage and the second tail passing through the second passage.

In Example 29, the subject matter of any one or more of Examples 24-28 optionally include a pin passing through the second intermediate portion proximate the post.

In Example 30, the subject matter of any one or more of Examples 24-29 optionally include a tube located proximate the post, the third and fourth tails passing through the tube.

In Example 31, the subject matter of any one or more of Examples 24-30 optionally include wherein the first suture is secured to the post.

In Example 32, the suture anchor constructs or methods of any one of or any combination of Examples 1-31 are optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

As disclosed herein, fixed sutures within an anchor can eliminate the need for a surgeon to tie knots for fixation. The free ends of the fixed sutures can be passed through soft tissue to a knotless anchor for a faster procedure. The suture constructs disclosed herein can include a fixed suture configuration where at least one suture is fixed to an anchor without a surgeon having to tie a knot or otherwise secure the suture to the anchor. As a result, the free ends of a suture can be passed through soft tissue and directly passed to a knotless anchor resulting in decreased time for a procedure. For example, the free ends of a fixed suture can be passed through the supraspinatus tendon, the subscapularis tendon, or the infraspinatus tendon during a rotator cuff repair procedure and then secured to each other using knots.

As used herein proximal refers to a location on a bone anchor that is closer to the physician. Distal refers to a location on a bone anchor that is away from the physician. Leading end refers to a tip or distal portion of a bone anchor. Trailing end refers to a tail or proximal portion of a bone anchor.

Figure 1:
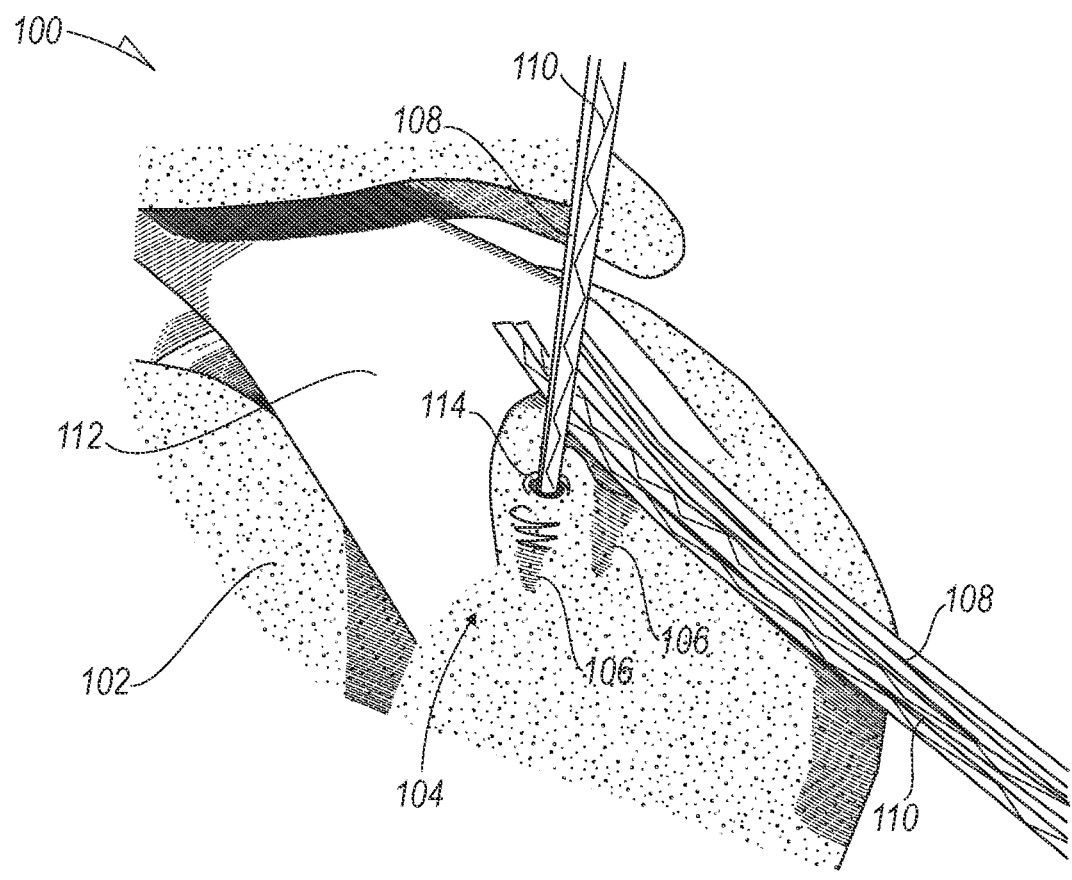
FIG. 1 shows a surgical site in accordance with at least one example of the present disclosure.

Turning now to the figures, FIG. 1 shows a surgical site 100 in accordance with at least one example of the present disclosure. As shown in FIG. 1, surgical site 100 can include a bone 102 in which one or more suture anchor constructs 104 may be implanted. Each of suture anchor constructs 104 can include an anchor 106, a first suture 108, and a second suture 110. Suture anchor constructs 104 can be used to secure tissue 112 to bone 102 as disclosed herein. Surgical site 100 can represent any surgical procedure where tissue can be attached to or otherwise anchored to bone.

Figure 2:
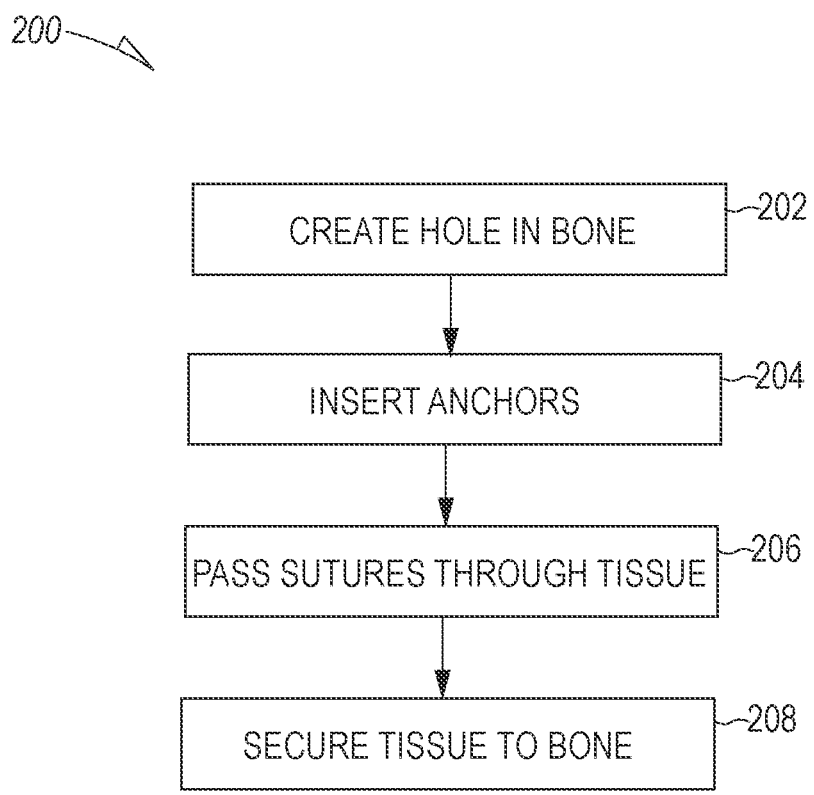
FIG. 2 shows a method in accordance with at least one example of the present disclosure.

FIG. 2 shows a method 200 for securing tissue to bone and will be described with reference to FIG. 1. During surgery, a surgeon can drill one or more holes 114 in bone 102 (202). Drilling holes 114 can include using a drill guide or other surgical instruments to locate holes 114 and/or sturdy the drilling equipment used to drill holes 114.

After holes 114 are drilled anchors 106 can be implanted into bone 102 (204). Implanting anchors 106 can include using an inserter to screw anchors 106, which can include a threaded exterior surface, into bone 102. Anchors 106 can also include barbs, a porous metal coating, and/or other features to secure anchors 106 within holes 104. Thus, anchors 106 can be pressed into bone 102 as well as screwed into bone 102.

With anchors 106 securely implanted into bone 102, any combination of first and second sutures 108 and 110 can be passed thought tissue 112 (206). Any one of second sutures 110, which are fixedly secured to a respective anchor 106, can be passed through tissue 112. As disclosed herein, the fixed nature of second suture 110 can allow the surgeon to secure tissue 112 to bone 102 without the need to first secure second suture 110 to anchors 106. First sutures 108 can also be passed through tissue 112 in preparation for securing tissue 112 to bone 102.

After passing at least one of first sutures 108 or second sutures 110 through tissue 112, tissue 112 can be secured to bone 102 (208). For example, using second sutures 110, which are now secured to bone 102 in an immovable manner, the surgeon can pull free ends of second sutures 110 to apply tension to tissue 112 and manipulate tissue 112 into a desired position. Once tissue 112 is in a desired position, the surgeon can tie the free ends of first and second sutures 108 and 110 together or to other sutures and/or anchors.

By having second sutures 110 secured to anchors 106, time can be saved in the operating room because the surgeon or other medical staff can pass seconds suture 110 through the tissue and have it anchored down with a knotless anchor, such as anchors 106, before inserting anchors 106. In addition, second sutures 110 being secured to anchors 106 can aid the surgeon in positioning tissue 112 due to the fixed nature of a portion of second suture 110.

Figure 3:
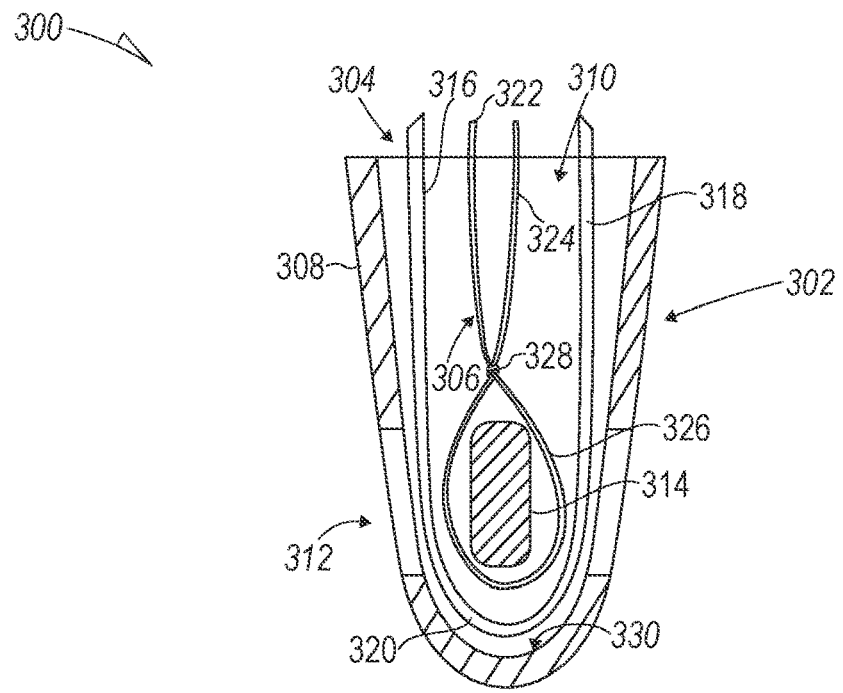
FIGS. 3-19B each shows a suture anchor construct in accordance with at least one example of the present disclosure.

FIG. 3 shows a suture anchor construct 300, such as suture anchor construct 100, in accordance with at least one example of the present disclosure. Suture anchor construct 300 can include an anchor 302, a first suture 304, and a second suture 306. Anchor 302 can include a body 308 that defines a central hole 310 and a radial hole 312. Anchor 302 can include a post 314 that extends from a first portion of radial hole 312 to a second portion of radial hole 312. Stated another way, post 314 can span from one side of anchor 302 to another side of anchor 302 within radial hole 312. Radial hole 312 and post 314 can be located proximate to the leading end of anchor 302.

First suture 304 can include a first tail 316, a second tail 318, and a first intermediate portion 320 located in between first tail 316 and second tail 318. Second suture 306 can include a third tail 322, a fourth tail 324, and a second intermediate portion 326 located in between third tail 322 and fourth tail 324.

Consistent with embodiments disclosed herein, first suture 304 can be free to move about post 314. By having first suture 304 being free to move, a surgeon can reposition first suture 304 as need. By repositioning first suture 304 the surgeon can adjust the lengths of first tail 316 and second tail 318 without having to cut first suture 304. The surgeon also has the option to tie knots if they want, or they can remove first suture 304 if they want.

Second suture 306 can be secured to post 314. As shown in FIG. 3, second intermediate portion 326 can be wrapped around post 314. A knot 328 can be tied in second intermediate portion 326 to fixedly secure second suture 306 to post 314. For example, knot 328 can be sliding or fixed hitch knot. Knot 328 can also be tied first first and anchor 302 can then be overmolded to form post 314 and secure second suture 306 to post 314.

By having second suture 306 secured to post 314, the surgeon can initially secure tissue to a bone, such as bone 102, in which anchor 302 can be implanted. The secured nature of second suture 306 can allow the surgeon to initially secure tissue, such as tissue 112, to a bone. For example, using second suture 306, the surgeon can pass fourth tail 324 through the tissue and manipulate fourth tail 324 to position the tissue. Fourth tail 324 can then be tied to third tail 322, first suture 304, bone, and/or other anatomical or implanted structures within the patient.

Tails 316, 318, 322, and 324 can be used to secure the tissue. For example, once the tissue is secured using fourth tail 324, the surgeon can then use first tail 316 and second tail 318 to further secure the tissue.

FIG. 3 shows first suture 304 located in between second suture 306 and an interior surface 330. This configuration can allow first suture 304 to move relative to post 314 and second suture 306.

Figure 4:
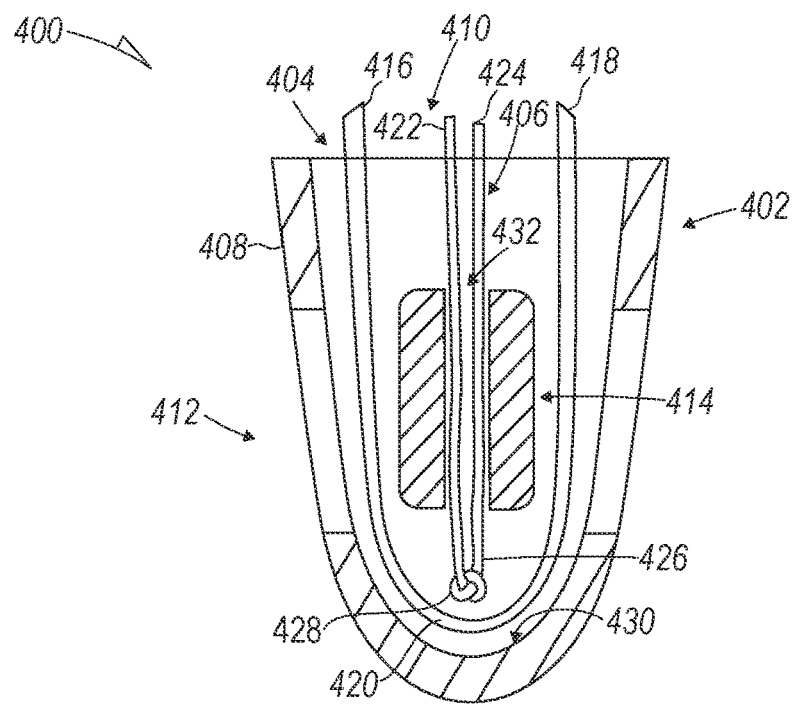

FIG. 4 shows a suture anchor construct 400 in accordance with at least one example of the present disclosure. Suture anchor construct 400 can include an anchor 402, a first suture 404, and a second suture 406. Anchor 402 can include a body 408 that defines a central hole 410 and a radial hole 412. Anchor 402 can include a post 414 that extends from a first portion of radial hole 412 to a second portion of radial hole 412. Post 414 can define a through-hole 432. Radial hole 412 and post 414 can be located proximate to a leading end of anchor 402.

First suture 404 can include a first tail 416, a second tail 418, and a first intermediate portion 420 located in between first tail 416 and second tail 418. Second suture 406 can include a third tail 422, a fourth tail 424, and a second intermediate portion 426 located in between third tail 422 and fourth tail 424. As shown in FIG. 4, first suture 404 can pass around post 414. In addition, first tail 416 and/or second tail 418 can pass through through-hole 432.

Consistent with embodiments disclosed herein, first suture 404 can be free to move about post 414 as disclosed above with respect to FIG. 4.

Second suture 406 can be secured to post 414. As shown in FIG. 4, second intermediate portion 426 can be tied into a knot 428. Knot 428 can be tied at a midpoint of second suture 406 or at any point along second suture 406.

The diameter of through-hole 432 can be smaller than the knot 428. As a result, knot 428 cannot pass back through through-hole 432. In other words, tension on third and fourth tails, 422 and 424, can cause knot 428 to become wedged in through-hole 432. While FIG. 4 shows through-hole 432 having a cylindrical profile, through-hole 432 can have a conical profile. Thus, as tension in third and fourth tails, 422 and 424, is increased, the force applied to knot 428 by the walls of through-hole 432 can increase.

By having second suture 406 secured to post 414, the surgeon can initially secure tissue to a bone, such as bone 102, in which anchor 402 can be implanted. The secured nature of second suture 406 can allow the surgeon to initially secure tissue, such as tissue 112, to a bone as disclosed above with respect to FIG. 3.

FIG. 4 shows first suture 404 located in between second suture 406 and an interior surface 430. This configuration can allow first suture 404 to move relative to post 414 and second suture 406 as disclosed above with respect to FIG. 3. Still consistent with embodiments disclosed herein, first suture 404 can be fixed to post 414. In addition, first suture 404 can pass through knot 428.

Figure 5:
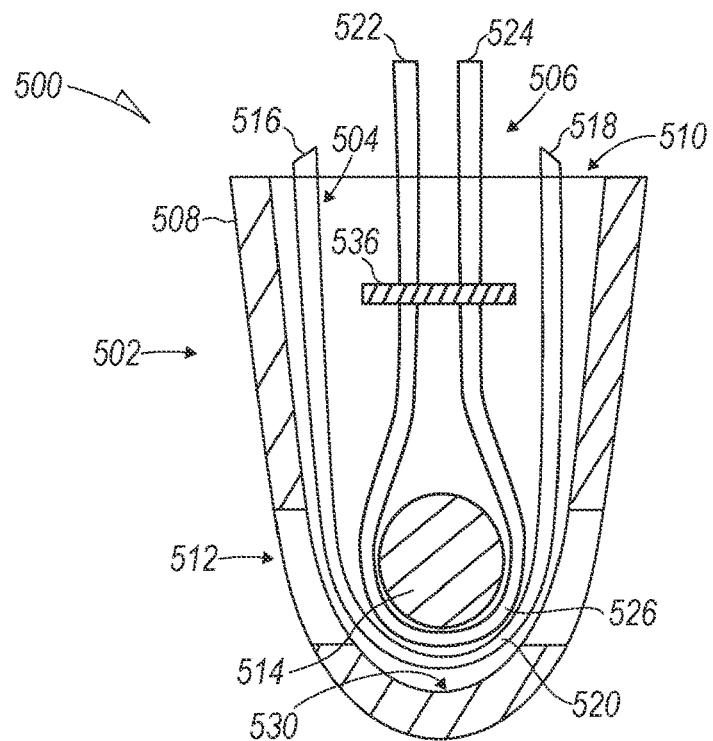

FIG. 5 shows a suture anchor construct 500 in accordance with at least one example of the present disclosure. Suture anchor construct 500 can include an anchor 502, a first suture 504, and a second suture 506. Anchor 502 can include a body 508 that defines a central hole 510 and a radial hole 512. Anchor 502 can include a post 514 that extends from a first portion of radial hole 512 to a second portion of radial hole 512. Radial hole 512 and post 514 can be located proximate to a leading end of anchor 502.

First suture 504 can include a first tail 516, a second tail 518, and a first intermediate portion 520 located in between first tail 516 and second tail 518. Second suture 506 can include a third tail 522, a fourth tail 524, and a second intermediate portion 526 located in between third tail 522 and fourth tail 524.

Consistent with embodiments disclosed herein, first suture 504 can be free to move about post 514 as disclosed above with respect to FIG. 3.

Second suture 506 can be secured to post 514. As shown in FIG. 5, second intermediate portion 526 can be wrapped around post 514. A pin 536 can pass through second intermediate portion 526 to fixedly secure second suture 506 to post 514.

By having second suture 506 secured to post 514, the surgeon can initially secure tissue to a bone, such as bone 102, in which anchor 502 can be implanted. The secured nature of second suture 506 can allow the surgeon to initially secure tissue, such as tissue 112, as disclosed above with respect to FIG. 3.

FIG. 5 shows first suture 504 located in between second suture 506 and an interior surface 530. This configuration can allow first suture 504 to move relative to post 514 and second suture 506 as disclosed above with respect to FIG. 3. Still consistent with embodiments disclosed herein, first suture 504 can be fixed to post 514. For example, pin 536 can pass through first suture 504 just as with second suture 506. In addition, a second pin (not shown) can pass through first suture 504 to second suture 506.

Figure 6:
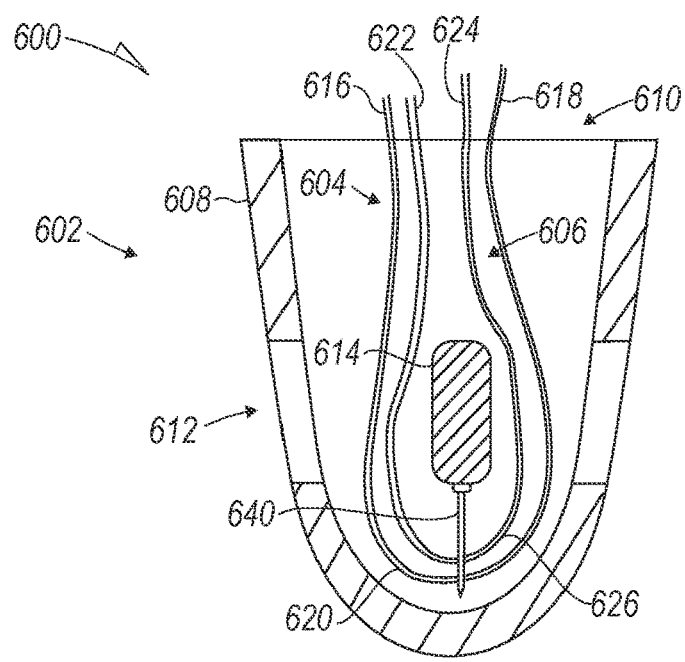

FIG. 6 shows a suture anchor construct 600 in accordance with at least one example of the present disclosure. Suture anchor construct 600 can include an anchor 602, a first suture 604, and a second suture 606. Anchor 602 can include a body 608 that defines a central hole 610 and a radial hole 612. Anchor 602 can include a post 614 that extends from a first portion of radial hole 612 to a second portion of radial hole 612. Radial hole 612 and post 614 can be located proximate to a leading end of anchor 602.

First suture 604 can include a first tail 616, a second tail 618, and a first intermediate portion 620 located in between first tail 616 and second tail 618. Second suture 606 can include a third tail 622, a fourth tail 624, and a second intermediate portion 626 located in between third tail 622 and fourth tail 624.

Consistent with embodiments disclosed herein, first suture 604 can be free to move about post 614 as disclosed above with respect to FIG. 3.

Second suture 606 can be secured to post 614. As shown in FIG. 6, post 614 can include a protrusion or barb 640. Barb 640 can extend from a distal side of post 614. Barb 640 can include a point that can allow barb 640 to pierce and pass through second suture 606. Still consistent with embodiments disclosed herein, second suture 606 can be tied to barb 640 instead of or in addition to being punctured by barb 640.

By having second suture 606 secured to post 614, the surgeon can initially secure tissue to a bone, such as bone 102, in which anchor 602 can be implanted. The secured nature of second suture 606 can allow the surgeon to initially secure tissue, such as tissue 112, as disclosed above with respect to FIG. 3.

First suture 604 can move relative to post 614 and second suture 606 as disclosed above with respect to FIG. 3. Still consistent with embodiments disclosed herein, first suture 604 can be fixed to post 614. For example, barb 640 can pass through first suture 604 or first suture 604 can be tied to barb 640 just as with second suture 606.

Figure 7:
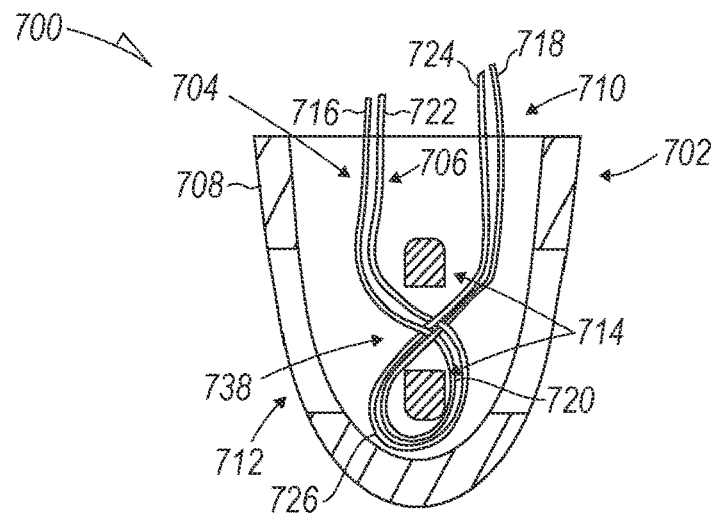

FIG. 7 shows a suture anchor construct 700 in accordance with at least one example of the present disclosure. Suture anchor construct 700 can include an anchor 702, a first suture 704, and a second suture 706. Anchor 702 can include a body 708 that defines a central hole 710 and a radial hole 712. Anchor 702 can include a post 714 that extends from a first portion of radial hole 712 to a second portion of radial hole 712. Radial hole 712 and post 714 can be located proximate to a leading end of anchor 702.

First suture 704 can include a first tail 716, a second tail 718, and a first intermediate portion 720 located in between first tail 716 and second tail 718. Second suture 706 can include a third tail 722, a fourth tail 724, and a second intermediate portion 726 located in between third tail 722 and fourth tail 724.

First suture 704 and second suture 706 can be secured to post 714. As shown in FIG. 7, post 714 can define a hole 738 which can divide post 714 into two portions. Tails 716, 718, 722, and 724 can be passed through hole 738 and wrapped around a distal portion of post 714. As shown in FIG. 7, first suture 704 and second suture 706 can be woven together to further secure first suture and second suture 706 to the distal portion of post 714.

By having first suture 704 and second suture 706 secured to post 714, the surgeon can initially secure tissue to a bone, such as bone 102, in which anchor 702 can be implanted. The secured nature of first suture 704 and second suture 706 can allow the surgeon to initially secure tissue, such as tissue 112, to a bone as disclosed above with respect to FIG. 3.

Figure 8:
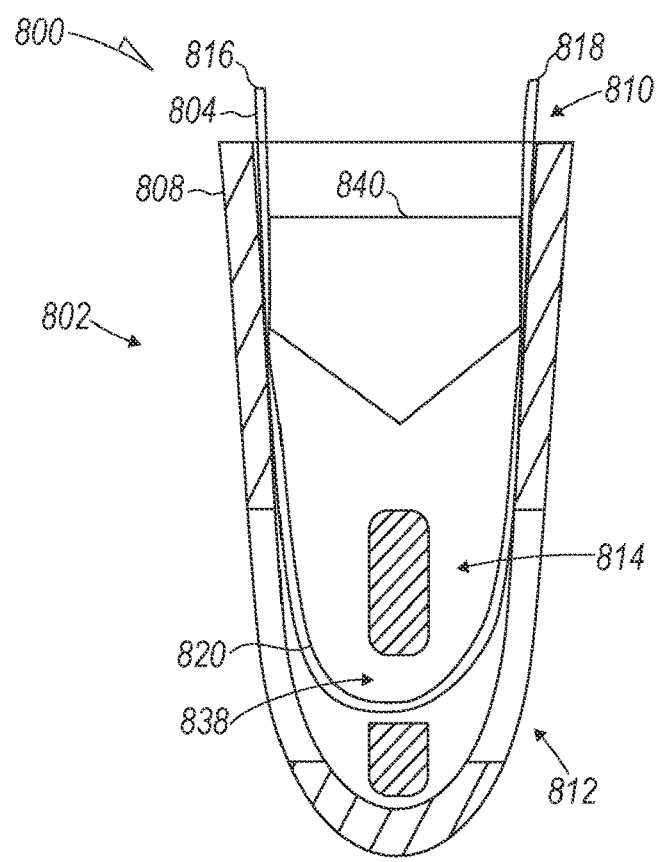

FIG. 8 shows a suture anchor construct 800 in accordance with at least one example of the present disclosure. Suture anchor construct 800 can include an anchor 802 and a first suture 804. Anchor 802 can include a body 808 that defines a central hole 810 and a radial hole 812. Anchor 802 can include a post 814 that extends from a first portion of radial hole 812 to a second portion of radial hole 812. Radial hole 812 and post 814 can be located proximate to a leading end of anchor 802.

First suture 804 can include a first tail 816, a second tail 818, and a first intermediate portion 820 located in between first tail 816 and second tail 818. While not shown, suture construct 800 can include a second suture as with other suture constructs disclosed herein.

First suture 804 can be secured to post 814. As shown in FIG. 8, post 814 can define a hole 838 which can divide post 814 into two portions. Tails 816 and 818 can be passed through hole 838 and wrapped around a proximal portion of post 814. In leu of a knot, a plug 840 can be inserted into central hole 810. Upon insertion of plug 840, plug 840 can become wedged into central hole 810. Friction between body 808, first suture 804 and plug 840 can secure first suture to anchor 802.

As disclosed herein, by having first suture 804 secured to post 814 the surgeon can initially secure tissue to a bone as disclosed above with respect to FIG. 3.

Figure 9:
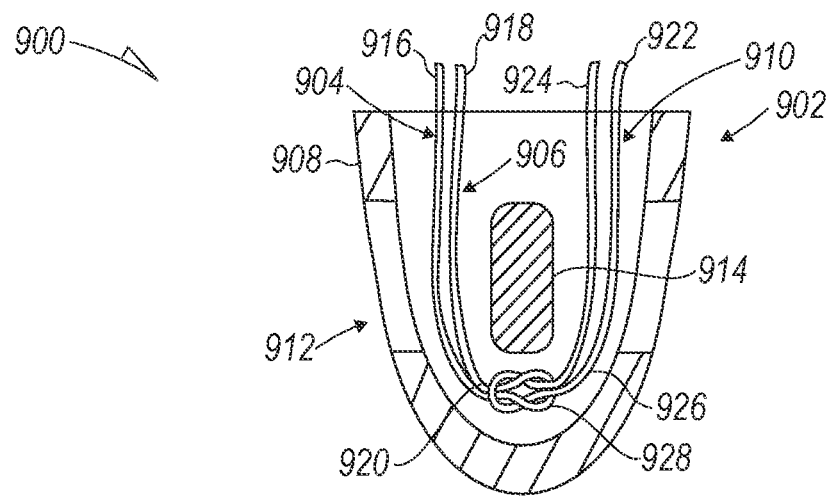

FIG. 9 shows a suture anchor construct 900 in accordance with at least one example of the present disclosure. Suture anchor construct 900 can include an anchor 902 and a first suture 904. Anchor 902 can include a body 908 that defines a central hole 910 and a radial hole 912. Anchor 902 can include a post 914 that extends from a first portion of radial hole 912 to a second portion of radial hole 912. Radial hole 912 and post 914 can be located proximate to a leading end of anchor 902.

First suture 904 can include a first tail 916, a second tail 918, and a first intermediate portion 920 located in between first tail 916 and second tail 918. Second suture 906 can include a third tail 922, a fourth tail 924, and a second intermediate portion 926 located in between third tail 922 and fourth tail 924.

First suture 904 can be secured to second suture 906. As shown in FIG. 9, first intermediate portion 920 and second intermediate portion 926 can be tied together. A knot 928 formed by tying first suture 904 and second suture 906 together can be located at a distal end of post 914. The configuration shown in FIG. 9 allows first suture 904 and second suture 906 to move relative to anchor 902, but not relative to one another.

Figure 10:
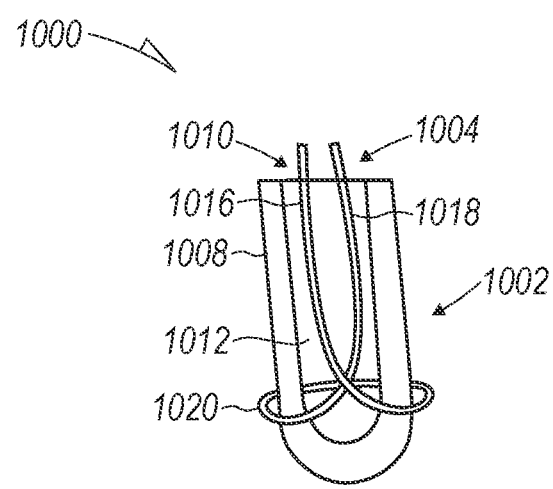

FIG. 10 shows a suture anchor construct 1000 in accordance with at least one example of the present disclosure. Suture anchor construct 1000 can include an anchor 1002 and a first suture 1004. Anchor 1002 can include a body 1008 that defines a central hole 1010 and a radial hole 1012. Radial hole 1012 and central hole 1010 can form an eyelet. The eyelet can be used to secure first suture 1004 to anchor 1002.

First suture 1004 can include a first tail 1016, a second tail 1018, and a first intermediate portion 1020 located in between first tail 1016 and second tail 1018. While not shown, suture construct 1000 can include a second suture or any number of sutures as with other suture constructs disclosed herein.

First suture 1004 can be secured to anchor 1002. As shown in FIG. 10, first intermediate portion 1020 can be wrapped around a distal portion of body 1008 to form a loop that can be located outside of anchor 1002. First tail 1016 and second tail 1018 can travel back through central hole 1010 and exit anchor 1002. When anchor 1002 is inserted into bone, first intermediate portion 1020 can be pinched in between body 1008 and the bone, thus locking first suture 1004 in a fixed portion.

Figure 11:
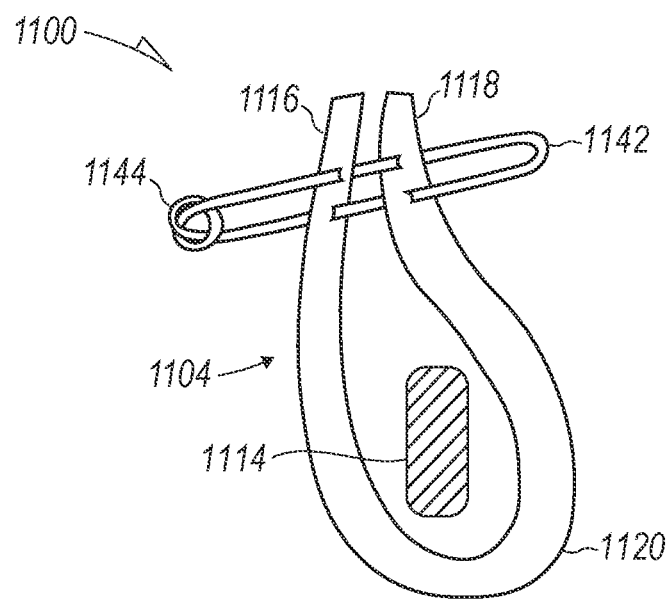

FIG. 11 shows a suture anchor construct 1100 in accordance with at least one example of the present disclosure. Suture anchor construct 1100 can include an anchor having a post 1114 (the anchor body is not shown) and a first suture 1104. The anchor can define a central hole and a radial hole as disclosed herein with respect to other anchors.

First suture 1104 can include a first tail 1116, a second tail 1118, and a first intermediate portion 1120 located in between first tail 1116 and second tail 1118. While not shown, suture construct 1100 can include a second suture or any number of sutures as with other suture constructs disclosed herein.

First suture 1104 can be secured to the anchor. As shown in FIG. 11, first intermediate portion 1120 can be wrapped around post 1114 and sewn together. For example, first intermediate portion 1120 can be wrapped around post 1114 and another short section of suture 1142 can pierced through both first tail 1116 and second tail 1118. After piercing first intermediate portion 1120, suture 1142 can be tied into a knot 1144 to secure first suture 1104 to post 1114.

The number of short sections of sutures 1142 can equal the number of regular sutures, such as first suture 1104, or be different. For example, a single short section of suture 1142 can pierce any number of regular sutures. In addition, each regular suture or groups of regular sutures can have their own respective short section of suture 1142.

Figure 12:
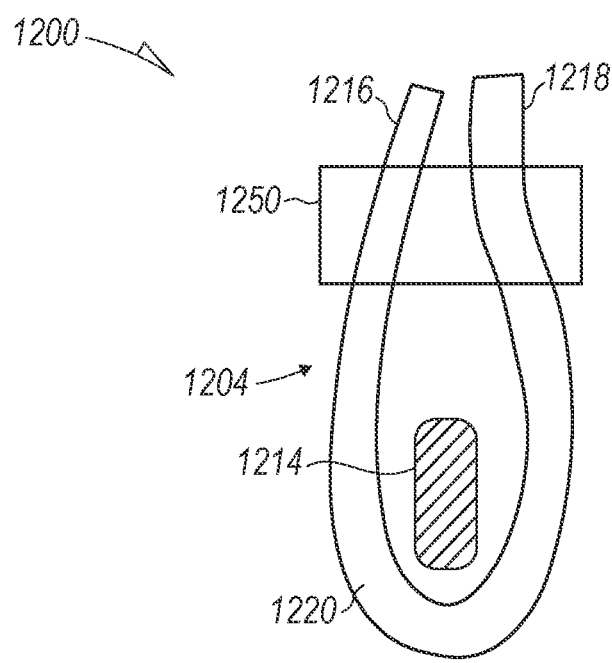

FIG. 12 shows a suture anchor construct 1200 in accordance with at least one example of the present disclosure. Suture anchor construct 1200 can include an anchor having a post 1214 (the anchor body is not shown) and a first suture 1204. The anchor can define a central hole and a radial hole as disclosed herein with respect to other anchors.

First suture 1204 can include a first tail 1216, a second tail 1218, and a first intermediate portion 1220 located in between first tail 1216 and second tail 1218. While not shown, suture construct 1200 can include a second suture or any number of sutures as with other suture constructs disclosed herein.

First suture 1204 can be secured to the anchor. As shown in FIG. 12, first intermediate portion 1220 can be wrapped around post 1214 and a tube 1250 can be used to secure first suture 1204 to post 1214. For example, first intermediate portion 1220 can be wrapped around post 1214 and both first tail 1216 and second tail 1218 can be fed through tube 1250. Tube 1250 can be tight fitting so as to maintain a position on first tail 1216 and second tail 1218 once placed thereon. To secure first suture 1204 to post 1214 tube 1250 can be pushed until it meets post 1214.

The number of tubes 1250 can equal the number of regular sutures, such as first suture 1204 or be different. For example, a tube 1250 can be located on any number of regular sutures. In addition, each regular suture or groups of regular sutures can have their own respective tube 1250.

Tube 1250 can be a rubber band type device. The rubber band type device can be attached to both first tail 1216 and second tail 1218. The rubber band type device can pull first tail 1216 and second tail 1218 together to prevent them from sliding.

Figure 13:
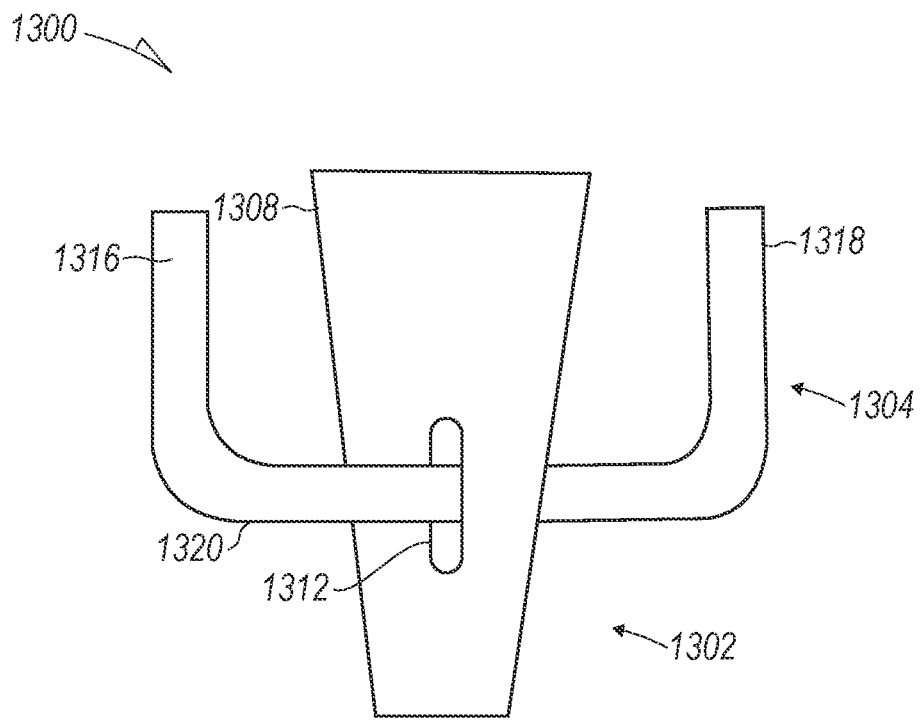

FIG. 13 shows a suture anchor construct 1300 in accordance with at least one example of the present disclosure. Suture anchor construct 1300 can include an anchor 1302 having a body 1308 that defines a radial hole 1312 and a first suture 1304.

First suture 1304 can include a first tail 1316, a second tail 1318, and a first intermediate portion 1320 located in between first tail 1316 and second tail 1318. While not shown, suture construct 1300 can include a second suture or any number of sutures as with other suture constructs disclosed herein.

First suture 1304 can be secured to anchor 1304. As shown in FIG. 13, first suture 1304 can be passed through radial hole 1312. Once anchor 1304 is implanted into bone, first suture 1304 can be compressed in between body 1308 and the bone. The compression of first suture 1304 can secure first suture 1304 into a fixed state.

Figure 14:
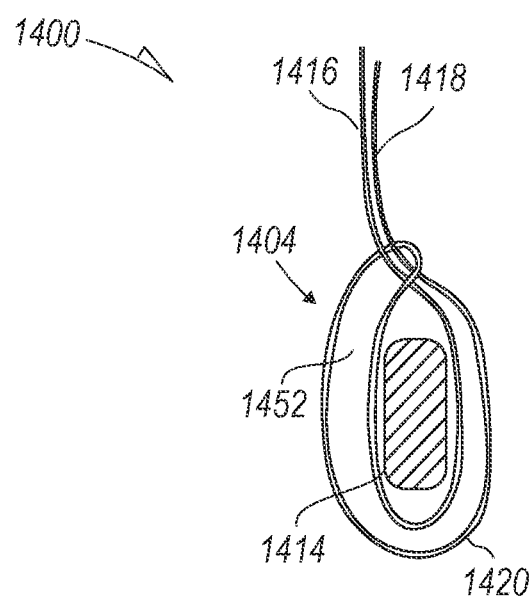

FIG. 14 shows a suture anchor construct 1400 in accordance with at least one example of the present disclosure. Suture anchor construct 1400 can include an anchor having a post 1414 (the anchor body is not shown) and a first suture 1404. The anchor can define a central hole and a radial hole as disclosed herein with respect to other anchors.

First suture 1404 can include a first tail 1416, a second tail 1418, and a first intermediate portion 1420 located in between first tail 1416 and second tail 1418. While not shown, suture construct 1400 can include a second suture or any number of sutures as with other suture constructs disclosed herein.

First suture 1404 can be secured to post 1414. As shown in FIG. 14, first intermediate portion 1420 can be wrapped around post 1414 and itself to secure first suture 1404 to post 1414. For example, first intermediate portion 1420 can be wrapped around post 1214 and both first tail 1216 and second tail 1218 can be fed through loop 1452 formed by first intermediate portion 1420. For instance, first suture 1404 can be folded in half to create loop 1452. Loop 1452 can then be wrapped around post 1414. First tail 1416 and second tail 1418 can then be passed through loop 1452.

The number of loops 1452 can equal the number of regular sutures, such as first suture 1404. For example, a loop 1452 can be formed for each regular suture. In addition, one or more regular sutures can be passed through a loop 1452 formed by a different suture. As a result, a single loop 1452 can be used to secure one or more sutures to post 1414.

Figure 15:
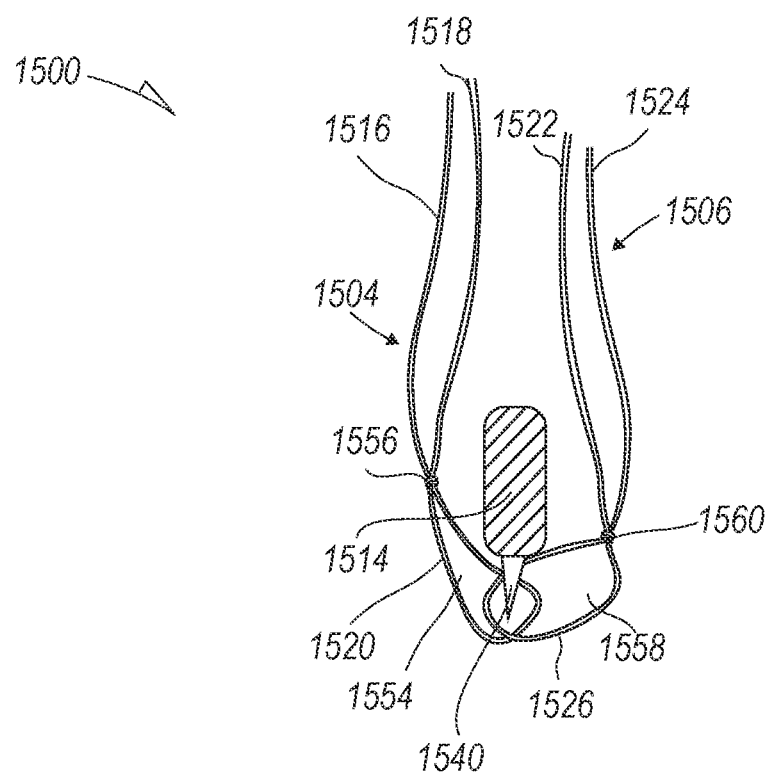

FIG. 15 shows a suture anchor construct 1500 in accordance with at least one example of the present disclosure. Suture anchor construct 1500 can include an anchor having a post 1514 (the anchor body is not shown), a first suture 1504, and a second suture 1506. Post 1514 can include a barb 1540 that protrudes from a distal portion of post 1514. The anchor can define a central hole and a radial hole as disclosed herein with respect to other anchors.

First suture 1504 can include a first tail 1516, a second tail 1518, and a first intermediate portion 1520 located in between first tail 1516 and second tail 1518. Second suture 1506 can include a third tail 1522, a fourth tail 1524, and a second intermediate portion 1526 located in between third tail 1522 and fourth tail 1544.

First suture 1504 and second suture 1506 can be secured to post 1514. As shown in FIG. 15, first intermediate portion 1520 can be folded to form a loop 1554 and a knot 1556 tied in first suture 1504. Second intermediate portion 1526 can be folded to form a loop 1558 and a knot 1560 tied in second suture 1506. Loops 1554 and 1558 can be placed around barb 1540 thus, securing first suture 1504 and second suture 1506 to the anchor. Knots 1556 and 1560 can be hitch knots or slip nots that allow loops 1554 and 1558 to collapse onto barb 1540 to prevent first suture 1504 and second suture 1506 from slipping off of barb 1540.

Figure 16:
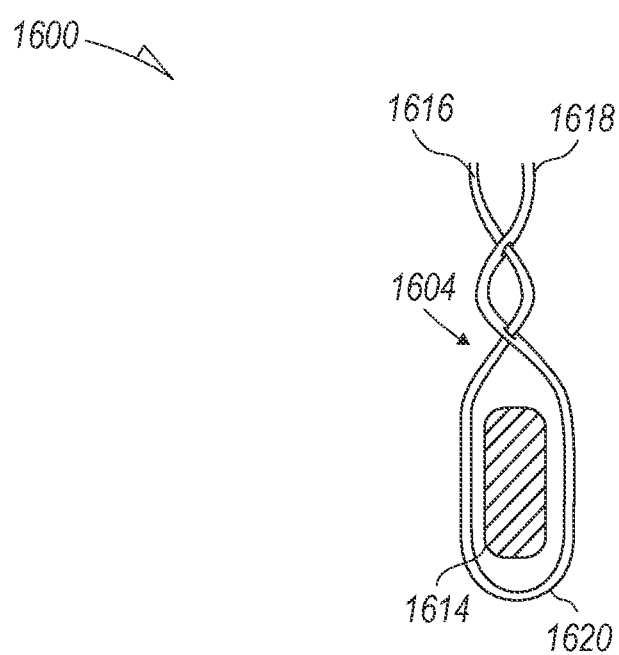

FIG. 16 shows a suture anchor construct 1600 in accordance with at least one example of the present disclosure. Suture anchor construct 1600 can include an anchor having a post 1614 (the anchor body is not shown) and a first suture 1604. The anchor can define a central hole and a radial hole as disclosed herein with respect to other anchors.

First suture 1604 can include a first tail 1616, a second tail 1618, and a first intermediate portion 1620 located in between first tail 1616 and second tail 1618. While not shown, suture construct 1400 can include a second suture or any number of sutures as with other suture constructs disclosed herein.

First suture 1604 can be secured to post 1614. As shown in FIG. 16, first intermediate portion 1620 can wrapped around post 1614. After wrapping first intermediate portion 1620 around post 1614, first tail 1616 can piece second tail 1618 one or more times to secure first suture 1604 to post 1614. While FIG. 16 shows a single suture, the number of sutures can be greater than one. Each of the sutures can be twisted together to both secure the sutures together and to post 1614. In addition, each suture can be twisted separately or in combination with a sub grouping of sutures.

Figure 17:
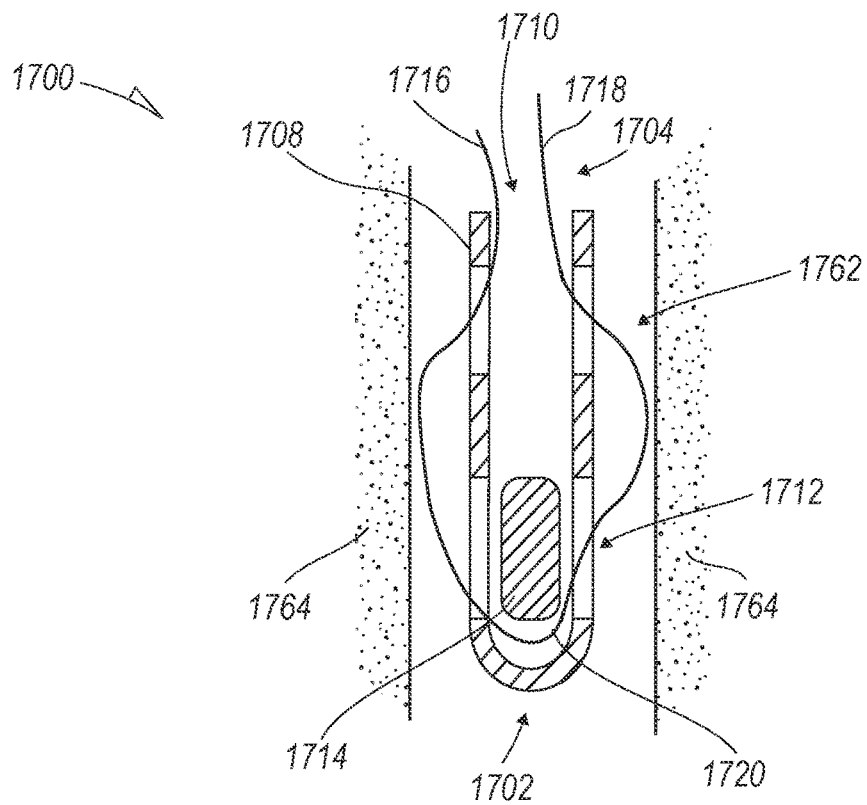

FIG. 17 shows a suture anchor construct 1700 in accordance with at least one example of the present disclosure. Suture anchor construct 1700 can include an anchor 1702 having a body 1708 and a post 1714 and a first suture 1704. The anchor can define a central hole 1710 and a first radial hole 1714 and a second radial hole 1762.

First suture 1704 can include a first tail 1716, a second tail 1718, and a first intermediate portion 1720 located in between first tail 1716 and second tail 1718. While not shown, suture construct 1700 can include a second suture or any number of sutures as with other suture constructs disclosed herein.

First suture 1704 and can be secured to post 1714. As shown in FIG. 17, first intermediate portion 1720 can wrap partially around a distal end of post 1714 and through first radial opening 1712. First tail 1716 and second tail 1718 can then re-enter central hole 1710 via second radial passage 1762 and exit anchor 1702. Once anchor 1702 is implanted in bone 1764, first suture 1704 can be compressed between bone 1764 and anchor 1702.

Figure 18:
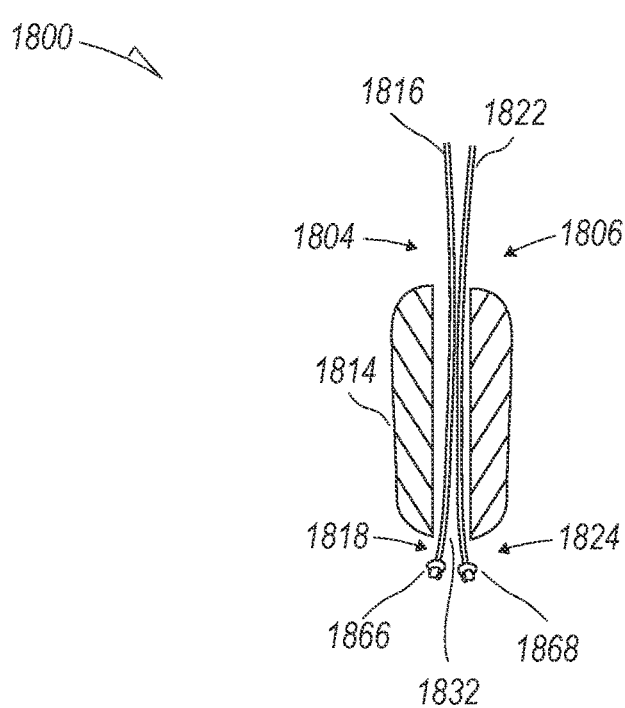

FIG. 18 shows a suture anchor construct 1800 in accordance with at least one example of the present disclosure. Suture anchor construct 1800 can include an anchor having a post 1814 (the anchor body is not shown), a first suture 1804, and a second suture 1806. The anchor can define a central hole and a radial hole as disclosed herein with respect to other anchors.

First suture 1804 can include a first tail 1816 and a second tail 1818 tied into a knot 1866. Second suture 1806 can include a third tail 1822 and a fourth tail 1824 tied into a knot 1868. The size of knots 1866 and 1868 are such that they will not fit through a through hole 1832. While FIG. 18 shows first suture 1804 and second suture 1806 tied individually, first suture 1804 and second suture 1806 can be tied together.

Figure 19A:
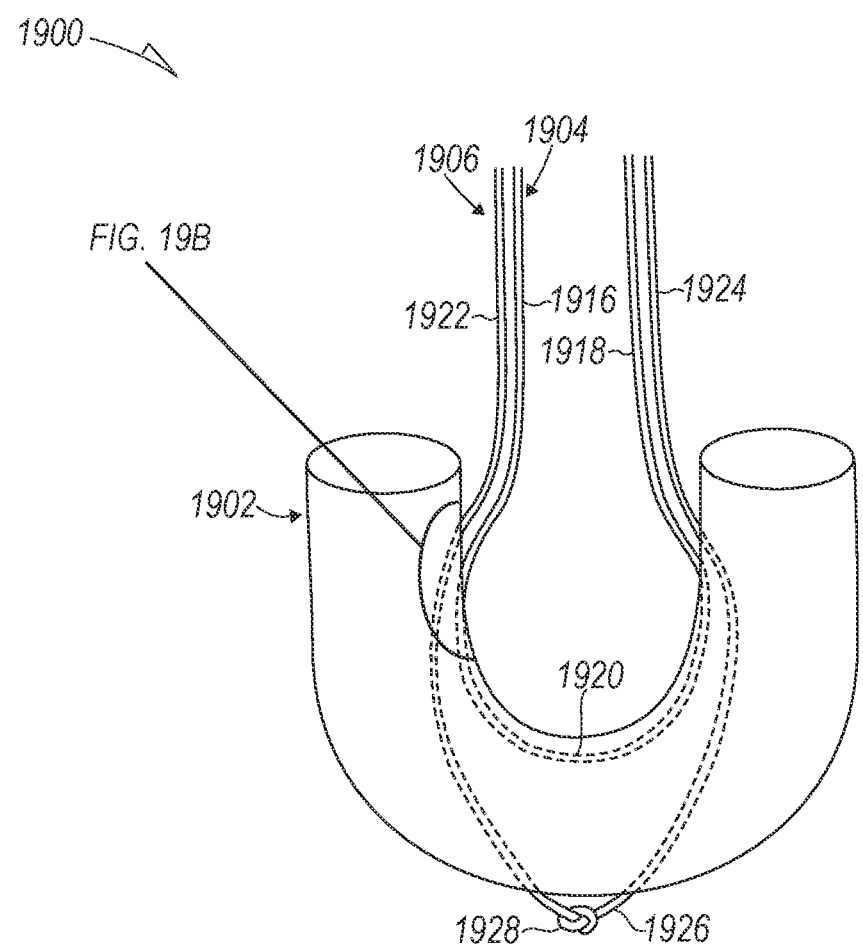

FIG. 19A shows a suture anchor construct 1900 in accordance with at least one example of the present disclosure. Suture anchor construct 1900 can include an anchor 1902, a first suture 1904, and a second suture 1906. First suture 1904 can include a first tail 1916, a second tail 1918, and a first intermediate portion 1920 located in between first tail 1916 and second tail 1918. Second suture 1906 can include a third tail 1922, a fourth tail 1924, and a second intermediate portion 1926 located in between third tail 1922 and fourth tail 1924.

Figure 19B:
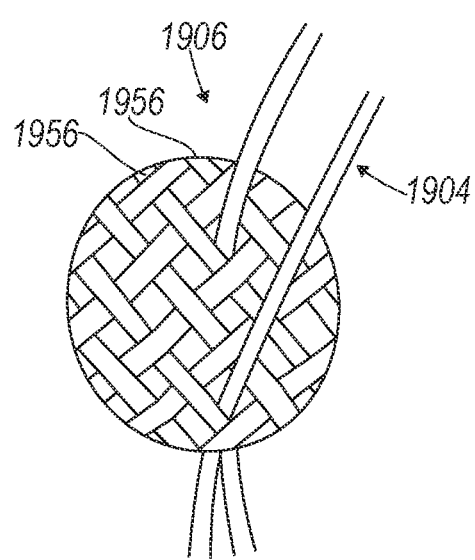

Anchor 1902 can be formed from a braided material, such as suture materials. As shown FIG. 19B, the braided material can be formed from a plurality of strands 1956. Also as shown in FIG. 19B, first suture 1904 and second suture 1906 can pass in between various strands 1954 to penetrate anchor 1902. To pass first suture 1904 and second suture 1906 in between the various strands 1954, a snare (not shown) can be used. The snare can include a wire that forms a loop or hook that can first be passed through anchor 1902. First suture 1904 and second suture 1906 can then be passed through the loop or hook of the snare and pulled through anchor 1902.

As shown in FIG. 19A, second intermediate portion 1926 can be tied into a knot 1928. Knot 1928 can secure second suture 1906 to anchor 1902. Knot 1928 can be bigger than the space between the various strands 1954 used to form anchor 1902. The larger size of knot 1928 can hinder movement of second suture 1906 upon implanting anchor 1902.

Suture anchor construct 1900 by passing first suture 1904 and second suture 1906 through anchor 1902 as described herein and forming knot 1928 to secure second suture 1906 to anchor 1902. Suture anchor construct 1900 can also be prepared by the manufacturer and delivered with first suture 1904 and second suture 1906 already connected to anchor 1902 with knot 1928 already formed to secure second suture 1906 to anchor 1902.

During surgery, the surgeon can use an inserter to press anchor 1902 into a hole drilled into bone. Upon extracting the inserter, anchor 1902 can remain in the hole and expand, thereby securing anchor 1902 in the hole. First tail 1916, a second tail 1918, third tail 1922, and a fourth tail 1924 can extend from the hole for use by the surgeon in securing tissue to the bone.

The various knots disclosed herein can be tied in a variety of fashions. The inserter used to install the anchors can be used to pull the knots tight. For example, a suture can be wrapped around the end of the inserter and pushed through a gap such as the central passage in the trailing end the anchor. The suture can include a pre-tied, but loose, knot located at the end of the inserter that is tightened using the inserter. Tightening the knot can create a suture anchor construct that is larger than the central passage in the anchor that the suture and inserter shaft are pushed through. The inserter can then be removed and the suture tied inside the anchor, unable to slide.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

What is claimed is:

1. A suture anchor construct, comprising:
   an anchor including an anchor body that defines a central hole extending from a trailing end of the anchor body along a central axis towards a leading end of the anchor body, the anchor further including a post located inside the anchor body;
   a first suture including a first tail, a second tail, and a first intermediate portion, the first intermediate portion extending around the post in an unfixed manner inside the anchor body with the first tail and the second tail extending back through the central hole and exiting the anchor body through the trailing end, the first intermediate portion slidable relative to the post such that the respective lengths of the first tail and the second tail are adjustable away from the trailing end; and
   a second suture including a third tail, a fourth tail, and a second intermediate portion, the second intermediate portion fixedly secured to the post such that the respective lengths of the third tail and the fourth tail that also extend back through the central hole and exit the anchor body through the trailing end are fixed,
   wherein the respective lengths of the first tail and the second tail can be adjusted away from the trailing end of the anchor body while the second intermediate portion of the second suture is fixedly secured to the post.

2. The suture anchor construct of claim 1, wherein the second intermediate portion is located in between the post and the first intermediate portion.

3. The suture anchor construct of claim 1, wherein the first intermediate portion is located in between the post and the second intermediate portion.

4. The suture anchor construct of claim 1, wherein the second intermediate portion fixedly secured to the post includes the second intermediate portion forming a hitch knot.

5. The suture anchor construct of claim 1, wherein the second intermediate portion fixedly secured to the post includes the second intermediate portion forming a loop that is wrapped around the post with the third tail and the fourth tail passing through the loop.

6. The suture anchor construct of claim 1, wherein the post defines a through hole, the second suture passing through the through hole and tied into a knot located at a distal end of the through hole.

7. The suture anchor construct of claim 1, wherein the post includes a first portion and a second portion located in between the first portion and the trailing end of the body, the second intermediate portion wrapped around the first portion.

8. The suture anchor construct of claim 1, wherein the second intermediate portion fixedly secured to the post includes the second intermediate portion partially surrounding the post.

9. The suture anchor construct of claim 1, further comprising a tube located proximate the post, the third tail and the fourth tail passing through the tube.

10. A suture anchor construct, comprising:
    an anchor including an anchor body and a post located inside the anchor body, the anchor body defining:
    a central hole extending from a trailing end of the anchor body along a central axis; and
    a radial hole located proximate a leading end of the anchor body and passing through the anchor body, the post extending from a first portion of the radial hole to a second portion of the radial hole;
    a first suture including a first tail, a second tail, and a first intermediate portion, the first intermediate portion slidably coupled to the post inside the anchor body such that the respective lengths of the first tail and the second tail are adjustable extending back through the central hole;
    and a second suture including a third tail, a fourth tail, and a second intermediate portion, the second intermediate portion forming a hitch knot that fixedly secures the second suture to the post inside the anchor body with the third tail and the fourth tail extending back through the central hole, wherein the respective lengths of the first tail and the second tail are adjustable while the second suture is secured to the post by the hitch knot.

11. The suture anchor construct of claim 10, wherein the second intermediate portion is located in between the post and the first intermediate portion.

12. The suture anchor construct of claim 10, wherein the hitch knot includes the second intermediate portion forming a loop that is wrapped around the post.

13. The suture anchor construct of claim 10, wherein the post defines a through hole, the second suture passing through the through hole, the hitch knot located at a distal end of the through hole.

* * * * *